US00PP21176P2

(12) United States Plant Patent
Smith

(10) Patent No.: US PP21,176 P2
(45) Date of Patent: Jul. 27, 2010

(54) ***CHRYSANTHEMUM* PLANT NAMED 'YOYOLANDA'**

(50) Latin Name: *Chrysanthemum×morifolium*
Varietal Denomination: Yoyolanda

(75) Inventor: Mark A. Smith, Fort Myers, FL (US)

(73) Assignee: Syngenta Crop Protection AG, Basel (CH)

( * ) Notice: Subject to any disclaimer, the term of this patent is extended or adjusted under 35 U.S.C. 154(b) by 0 days.

(21) Appl. No.: 12/459,534

(22) Filed: Jul. 2, 2009

(51) Int. Cl.
*A01H 5/00* (2006.01)

(52) U.S. Cl. ..... Plt./289

(58) Field of Classification Search ..... Plt./289
See application file for complete search history.

*Primary Examiner*—June Hwu
(74) *Attorney, Agent, or Firm*—S. Matthew Edwards

(57) ABSTRACT

A new *Chrysanthemum* plant named 'Yoyolanda,' particularly distinguished by the medium to large yellow decorative-type inflorescence; upright, mounded and compact plant habit that is freely branching; and medium to dark green foliage.

1 Drawing Sheet

Latin name of the genus and species of the plant claimed: *Chrysanthemum×morifolium.*

Varietal denomination: 'Yoyolanda'.

BACKGROUND OF THE NEW PLANT

The present invention comprises a new *Chrysanthemum*, botanically known as *Chrysanthemum×morifolium*, and hereinafter referred to by the variety name 'Yoyolanda'.

'Yoyolanda' is a product of a planned breeding program. The new cultivar has medium to large yellow decorative-type inflorescence; upright, mounded and compact plant habit that is freely branching; and medium to dark green foliage.

'Yoyolanda' originated from a hybridization made in January 2005 in a controlled breeding program in Salinas, Calif. 'Yoyolanda' was selected as a single flowering plant within the progeny of the stated cross in October 2005 in a controlled environment in Alva, Fla.

The female parent was the proprietary plant designated 'Gedi One Ces' (Cesaro), U.S. Plant Pat. No. 13,797 with larger, more golden-yellow flower color; slightly lighter colored foliage with a larger plant habit.

The male parent of 'Yoyolanda' was an unpatented hybrid seedling identified as '00-M389' with lavender flower color. '00-M389' has a smaller plant habit and a faster natural flowering response than 'Yoyolanda'.

The first act of asexual reproduction of 'Yoyolanda' was accomplished when vegetative cuttings were propagated from the initial selection in December 2005 in a controlled environment in Alva, Fla.

BRIEF SUMMARY OF INVENTION

Horticultural examination of plants grown from cuttings of the plant initiated in December 2005, and continuing thereafter, has demonstrated that the combination of characteristics as herein disclosed for 'Yoyolanda' are firmly fixed and are retained through successive generations of asexual reproduction.

'Yoyolanda' has not been observed under all possible environmental conditions. The phenotype may vary significantly with variations in environment such as temperature, light intensity and day length.

The following traits have been repeatedly observed and are determined to be basic characteristics of the new variety. The combination of these characteristics distinguishes this *Chrysanthemum* as a new and distinct variety.

Plant Breeder's Rights for this cultivar have not been applied for. 'Yoyolanda' has not been made publicly available more than one year prior to the filing of this application.

BRIEF DESCRIPTION OF THE PHOTOGRAPHS

The accompanying photographic drawing shows typical flower and foliage characteristics of 'Yoyolanda' with colors being as true as possible with an illustration of this type. The photographic drawing shows a flowering potted plant of the new variety and a close-up of the flowers.

DETAILED BOTANICAL DESCRIPTION

The plant description and measurements were taken in Salinas, Calif. in late May 2009 under natural light, and the aforementioned photographs were taken in Gilroy, Calif. in late May 2009 in a greenhouse.

These plants were started and grown in six inch pots, in Alva, Fla. and were shipped in mid-May 2009 to California. Plants were grown under conditions which approximate those generally used in commercial potted *Chrysanthemum* production, including the use of short day/long night treatments and the pinching of terminal apices. These plants used in the photograph and descriptions were about ten weeks old.

Color references are made to The Royal Horticultural Society Colour Chart (R.H.S.) 2001.

TABLE 1

DIFFERENCES BETWEEN THE NEW VARIETY 'YOYOLANDA' AND A SIMILAR VARIETY

| | 'Yoyolanda' | 'Janice' (U.S. Plant Pat. No. 9,817) |
|---|---|---|
| Flower size: | Little larger | Little smaller |
| Plant habit: | Little and rounder | Little taller and less round |
| Flower lastingness: | Longer than | Shorter than |

Plant:
*Form, growth and habit.*—Herbaceous decorative garden-type. Stems upright and outwardly spreading, freely branching, strong and moderately vigorous growth habit.
*Plant height.*—22-24 cm.
*Plant height (inflorescence included).*—24-26 cm.
*Plant width.*—35-40 cm.
*Garden performance and tolerance to weather.*—Good.
*Crop time to flowering.*—About 40-46 days.

Roots:
*Number of days to initiate roots.*—4 days at about 21 degrees C.
*Number of days to produce a rooted cutting.*—10-12 days at 21 degrees C.
*Type.*—Fine, fibrous, free branching.
*Color.*—RHS N155B but whiter.

Foliage:
*Arrangement.*—Alternate, simple.
*Immature, leaf color, upper surface.*—Closest to RHS 137A.
*Lower surface.*—RHS 147B.
*Mature, leaf color, upper surface.*—Closest to RHS 147A but a little lighter.
*Lower surface.*—RHS 147B.
*Length.*—5.7-6.2 cm.
*Width.*—4.0-4.4 cm.
*Shape.*—Ovate.
*Base shape.*—Attenuate.
*Apex shape.*—Mucronulate.
*Margin.*—Palmately lobed, slightly incised and serrate.
*Texture, upper surface.*—Bifid T-shaped hairs.
*Lower surface.*—Bifid t-shaped hairs.
*Color of veins, upper surface.*—RHS 146D.
*Color of veins, lower surface.*—RHS 146D.
*Petiole color.*—RHS 146D.
*Length.*—1.9-2.2 cm.
*Diameter.*—0.2 cm.
*Texture.*—Bifid T-shaped hairs.

Stem:
*Quantity of main branches per plant, after removal of terminal apex (pinching).*—5-7.
*Quantity of leaves per branch.*—About 10-12.
*Color of stem.*—Between RHS 146A and RHS 146B.
*Length of stem.*—16-19 cm.
*Diameter.*—0.3-0.45 cm.
*Length of internodes.*—1-3 cm.
*Texture.*—Heavily covered with Bifid T-shaped hairs.
*Color of peduncle.*—Between RHS 146A and RHS 146B.
*Length of peduncle.*—3.5-4.5 cm.
*Peduncle diameter.*—0.2 cm.
*Texture.*—Heavily covered with Bifid T-shaped hairs.

Inflorescence:
*Type.*—Compositate type, solitary inflorescences (decorative-type) borne terminally above foliage, ray florets arranged acropetally on a capitulum.
*Blooming habit.*—Natural season flowering around mid September.
*Average quantity of inflorescences per plant.*—100.
*Average quantity of inflorescences per lateral stem.*—About 30.
*Lastingness of individual blooms on the plant.*—About 4 weeks.
*Fragrance.*—Slightly spicy.

Bud (just before opening/showing color):
*Color.*—RHS 9A.
*Length.*—0.8-1.0 cm.
*Width.*—0.9-1.1 cm.
*Shape.*—Oblate.

Immature inflorescence:
*Diameter.*—3.5 cm.
*Color of ray florets, upper surface.*—RHS 6A with RHS 7B apex.
*Lower surface.*—RHS 6B.

Mature inflorescence:
*Diameter.*—5.4-5.8 cm.
*Depth.*—1.5 cm.
*Total diameter of 'disc'.*—Cannot see disc florets.
*Recepticle height.*—0.4 cm.
*Receptacle diameter.*—0.4-0.5 cm.

Ray florets:
*Average quantity of florets.*—About 150 in numerous whorls.
*Color of florets, upper surface.*—RHS 6B.
*Lower surface.*—Between RHS 4A and RHS 4B.
*Length.*—1.3-2.8 cm.
*Width.*—0.5-0.6 cm.
*Shape.*—Narrowly elliptical when young to more oblong when mature.
*Apex shape.*—Slightly praemorse.
*Margin.*—Entire.
*Texture, upper surface.*—Papillose.
*Lower surface.*—Papillose.

Disc florets:
*Average quantity of florets.*—About 7, very immature, and irregularly spaced on recepticle.
*Color of florets.*—Closest to RHS 155D, but translucent.
*Length.*—Less than 0.1 cm.
*Width.*—Less than 0.1 cm.
*Shape.*—Tubular.
*Apex shape.*—5-pointed.

Phyllaries:
*Quantity.*—18-21.
*Color, upper surface.*—Closest to RHS 137A.
*Lower surface.*—Closest to RHS 137A.
*Length.*—0.6-0.7 cm.
*Width.*—0.15-0.2 cm.
*Shape.*—Lanceolate.
*Apex shape.*—Acute.
*Base.*—Fused.
*Margins.*—Entire, papery and translucent.
*Texture, upper surface.*—Glossy and smooth.
*Lower surface.*—Bifid T-shaped hairs.

Reproductive organs:
*Gynoecium.*—Found on both florets.
*Pistil quantity.*—1.
*Length.*—0.3 cm.
*Style color.*—RHS 155C.
*Style length.*—0.2 cm.
*Stigma color.*—RHS 3B.
*Stigma shape.*—Bi-parted.
*Ovary color.*—About RHS 157B.
*Androecium.*—Found on only disc florets.
*Stamen quantity.*—4-5.
*Color of filaments.*—RHS 155C.
*Length filaments.*—Less than 0.1 cm.
*Anther color.*—About RHS 17B.
*Anther length.*—About 0.15 cm.
*Anther shape.*—Ligulate.

*Color of pollen.*—About RHS 2D.

*Pollen amount.*—Very scarce.

*Fertility/seed set.*—Has not been observed on this hybrid.

Disease/pest resistance: Disease resistance or susceptibility has not been observed on this hybrid.

What is claimed is:

1. A new and distinct variety of *Chrysanthemum* plant named 'Yoyolanda,' substantially as illustrated and described herein.

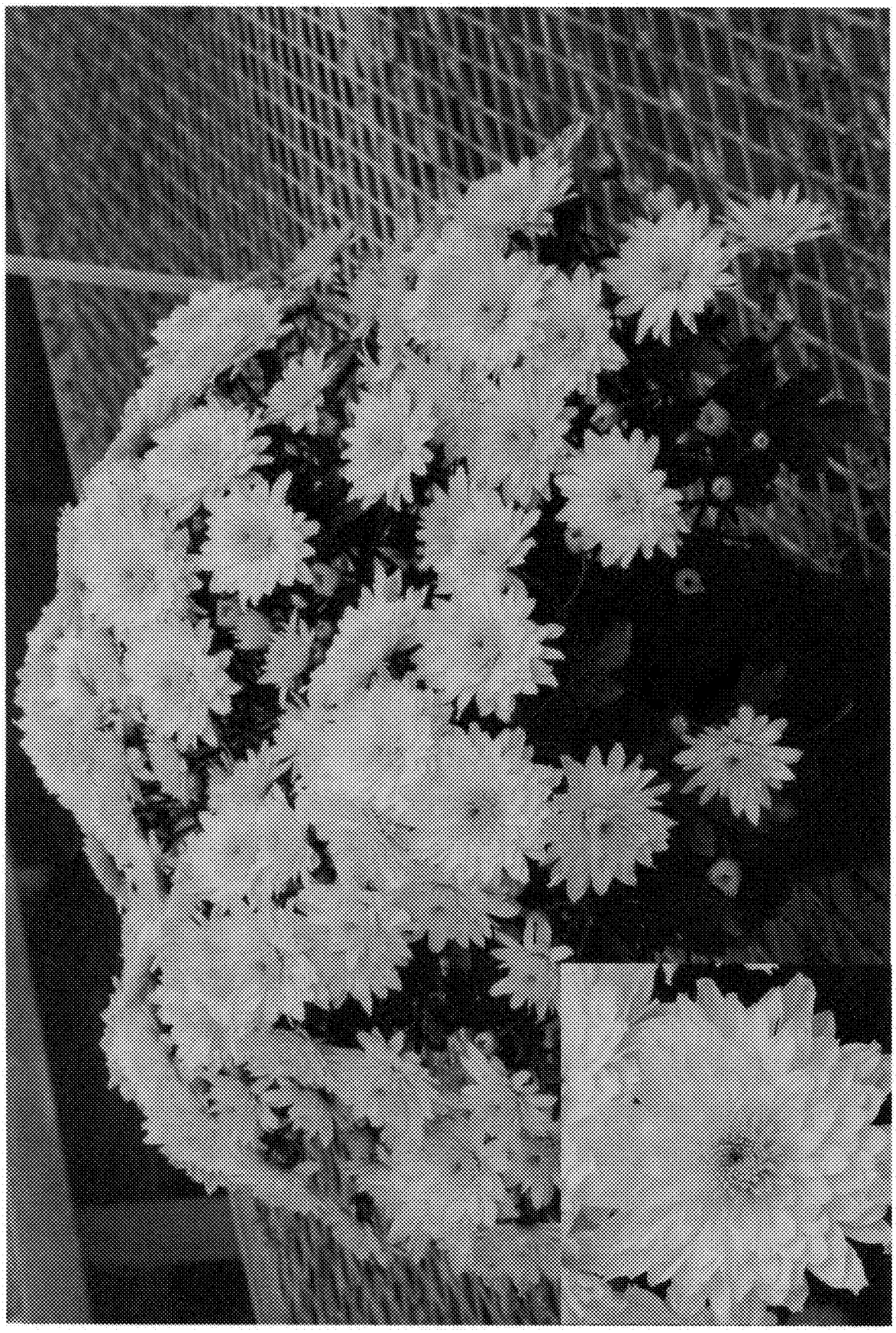

* * * * *